(12) United States Patent
Morimoto et al.

(10) Patent No.: US 11,039,739 B2
(45) Date of Patent: Jun. 22, 2021

(54) ENDOSCOPE SYSTEM

(71) Applicant: FUJIFILM Corporation, Tokyo (JP)

(72) Inventors: Yoshinori Morimoto, Kanagawa (JP); Eiji Ohashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 271 days.

(21) Appl. No.: 16/055,168

(22) Filed: Aug. 6, 2018

(65) Prior Publication Data

US 2019/0038119 A1    Feb. 7, 2019

(30) Foreign Application Priority Data

Aug. 7, 2017 (JP) .............................. JP2017-152239

(51) Int. Cl.
*A61B 1/00* (2006.01)
*A61B 1/06* (2006.01)
(Continued)

(52) U.S. Cl.
CPC .............. *A61B 1/0684* (2013.01); *A61B 1/04* (2013.01); *A61B 1/0638* (2013.01);
(Continued)

(58) Field of Classification Search
None
See application file for complete search history.

(56) References Cited

U.S. PATENT DOCUMENTS

| 2005/0010081 A1 | 1/2005 | Doguchi et al. |
| 2007/0090271 A1 | 4/2007 | Kobayashi |

(Continued)

FOREIGN PATENT DOCUMENTS

| JP | S62067512 | 3/1987 |
| JP | 2007111338 | 5/2007 |

(Continued)

OTHER PUBLICATIONS

"Search Report of Europe Counterpart Application", dated Dec. 7, 2018, p. 1-p. 8.

(Continued)

*Primary Examiner* — Timothy J Neal
(74) *Attorney, Agent, or Firm* — JCIPRNET

(57) ABSTRACT

There is provided an endoscope system capable of maintaining a constant light amount ratio for each wavelength of light emitted from an endoscope.
The endoscope system has: an endoscope that has a light guide; two or more light sources that supply light to the light guide and have different main wavelengths; a light source driving unit that supplies a driving signal to each of the light sources; a light source control unit that makes the light source driving unit generate a driving signal corresponding to the light amount setting value; and a light source information storage unit that stores information of the main wavelength. The endoscope has a scope information storage unit that stores information of a scope type. The light source control unit adjusts a light amount ratio of the light source to a preset light amount ratio by acquiring the information of the main wavelength of the light source from the light source information storage unit, acquiring the information of the scope type from the scope information storage unit, setting the light amount setting value according to at least the information of the main wavelength and information of a length of the light guide obtained from the information of the scope type, and inputting the light amount setting value to the light source driving unit to control a light emission amount of the light source driven by the light source driving unit.

12 Claims, 6 Drawing Sheets

(51) Int. Cl.
*A61B 1/04* (2006.01)
*G02B 23/24* (2006.01)
(52) U.S. Cl.
CPC .......... *A61B 1/0646* (2013.01); *A61B 1/0676* (2013.01); *G02B 23/2461* (2013.01)

(56) References Cited

U.S. PATENT DOCUMENTS

| | | | |
|---|---|---|---|
| 2011/0034770 A1* | 2/2011 | Endo | A61B 1/0019 600/118 |
| 2011/0069163 A1 | 3/2011 | Ozawa et al. | |
| 2011/0237885 A1* | 9/2011 | Matsubara | A61B 1/063 600/109 |
| 2012/0253122 A1 | 10/2012 | Minetoma et al. | |
| 2019/0117041 A1* | 4/2019 | Tanaka | A61B 1/0002 |
| 2020/0060530 A1* | 2/2020 | Yabe | A61B 1/0002 |

FOREIGN PATENT DOCUMENTS

| | | | |
|---|---|---|---|
| JP | 2010158413 | 7/2010 | |
| JP | 2011036361 | 2/2011 | |
| JP | 2012213612 | 11/2012 | |
| JP | 2013202166 A * | 10/2013 | ............... A61B 1/00 |

OTHER PUBLICATIONS

"Office Action of Japan Counterpart Application" with English translation thereof, dated Dec. 15, 2020, p. 1-p. 15.
Office Action of Japan Counterpart Application, with English translation thereof, dated Aug. 11, 2020, pp. 1-11.

* cited by examiner

ENDOSCOPE SYSTEM

CROSS-REFERENCE TO RELATED APPLICATIONS

The present application claims priority under 35 U.S.C. § 119 to Japanese Patent Application No. 2017-152239, filed on Aug. 7, 2017. The above application is hereby expressly incorporated by reference, in its entirety, into the present application.

BACKGROUND OF THE INVENTION

1. Field of the Invention

The present invention relates to an endoscope system.

2. Description of the Related Art

In recent medical treatments, diagnosis and the like using an endoscope system including a light source device for an endoscope, an electronic endoscope (endoscope), and a processor device have been widely performed. The light source device for an endoscope generates illumination light and emits the illumination light to the inside of a subject. The electronic endoscope generates an image signal by imaging the inside of the subject, to which the illumination light is emitted, using an imaging element. The processor device generates an observation image to be displayed on a monitor by performing image processing on the image signal generated by the electronic endoscope.

In a known light source device for an endoscope, a lamp light source, such as a xenon lamp or a halogen lamp that emits white light as illumination light, is used. In recent years, however, a semiconductor light source, such as a laser diode (LD) or a light emitting diode (LED) that emits light of specific color, is used instead of the lamp light source (for example, refer to JP2010-158413A).

In the light source device for an endoscope disclosed in JP2010-158413A, a first LED that emits red light, a second LED that emits green light, and a third LED that emits blue light are provided as semiconductor light sources for an endoscope, and light beams of three colors emitted from the first to third LEDs are combined to generate white light. In a light source device for an endoscope including a lamp light source, it is not possible to change the proportion of each color component in the illumination light. However, in a light source device for an endoscope having a plurality of semiconductor light sources, it is possible to change the proportion of each color component in the illumination light by independently controlling the light emission amount of each semiconductor light source. Therefore, adjustment of the color temperature of the illumination light and the like can be easily performed.

Incidentally, in the endoscope system, the endoscope is configured to be detachable from the light source device for an endoscope and the processor device, so that one of different kinds of endoscopes is appropriately connected to the light source device for an endoscope and the processor device depending on a difference in an observation part or the like.

In this case, the light transmission characteristic (transmittance) differs depending on a difference in the thickness of a light guide for each endoscope and the like. For this reason, in a case where the light emission amount of each light source is the same, the brightness of illumination light changes for each endoscope. Therefore, JP2007-111338A discloses an endoscope apparatus capable of adjusting the amount of light, which is emitted from an endoscope connected to a processor according to the light transmission characteristic of a light guide in the endoscope, based on scope identification information.

SUMMARY OF THE INVENTION

Here, according to the studies of the present inventors, it has been found out that, in a case where different kinds of endoscopes are used, there is a problem that the color of light changes as well as the change in the amount of light emitted from the endoscope.

It has been found out that the color change is due to a difference in the amount of change in the transmittance of the light guide depending on the wavelength of light. Specifically, as the wavelength becomes shorter, the amount of change in the transmittance depending on the length of the light guide becomes larger. In a case where the length of the light guide is large, a rate at which the transmittance decreases on the short wavelength side is larger than a rate at which the transmittance decreases on the long wavelength side. Therefore, due to the difference in the length of the light guide, the light amount ratio (proportion of each color component) for each wavelength of light emitted from the endoscope changes and the color changes.

In a case where the color of the light emitted from the endoscope is changed, there is a problem that the color of an observation image captured by the endoscope is changed.

It is an object of the invention to provide an endoscope system capable of maintaining a constant light amount ratio for each wavelength of light emitted from an endoscope.

As a result of intensive studies to solve the aforementioned problems, the present inventors have found out that the above problems can be solved as follows, and completed the invention. Specifically, an endoscope system comprises: an endoscope that has a light guide for guiding light; two or more light sources that supply light to the light guide and have different main wavelengths; a light source driving unit that supplies a driving signal to each of the two or more light sources to emit light; a light source control unit that inputs a light amount setting value to the light source driving unit to make the light source driving unit generate the driving signal corresponding to the light amount setting value; and a light source information storage unit that stores information of the main wavelength of at least one of the two or more light sources. The endoscope has a scope information storage unit that stores information of a scope type. The light source control unit adjusts a light amount ratio in light emitted from the endoscope to a preset light amount ratio by acquiring the information of the main wavelength of the light source from the light source information storage unit, acquiring the information of the scope type from the scope information storage unit, setting at least one light amount setting value according to at least the information of the main wavelength and information of a length of the light guide obtained from the information of the scope type, and inputting the light amount setting value to the light source driving unit to control a light emission amount of the light source driven by the light source driving unit.

That is, the present inventors have found out that the aforementioned problems can be solved by the following configurations.

[1] An endoscope system comprises: an endoscope that has a light guide for guiding light; two or more light sources that supply light to the light guide and have different main wavelengths; a light source driving unit that supplies a driving signal to each of the two or more light sources to emit light; a light source control unit that inputs a light amount setting value to the light source driving unit to make the light source driving unit generate the driving signal corresponding to the light amount setting value; and a light source information storage unit that stores information of the main wavelength of at least one of the two or more light sources. The endoscope has a scope information storage unit that stores information of a scope type. The light source control unit adjusts a light amount ratio in light emitted from the endoscope to a preset light amount ratio by acquiring the information of the main wavelength of the light source from the light source information storage unit, acquiring the information of the scope type from the scope information storage unit, setting at least one light amount setting value according to at least the information of the main wavelength and information of a length of the light guide obtained from the information of the scope type, and inputting the light amount setting value to the light source driving unit to control a light emission amount of the light source driven by the light source driving unit.

[2] The endoscope system described in [1], in which the endoscope has an illumination lens disposed on a distal end side of the light guide and the light source control unit sets the light amount setting value according to at least the information of the length of the light guide, information of the illumination lens obtained from the information of the scope type, and the information of the main wavelength of the light source.

[3] The endoscope system described in [1] or [2], in which the light source control unit sets the light amount setting value according to at least the information of the length of the light guide, information of a type of the light guide obtained from the information of the scope type, and the information of the main wavelength of the light source.

[4] The endoscope system described in any one of [1] to [3], in which at least one of the two or more light sources is a blue light source that emits blue light and the light source control unit sets the light amount setting value for the blue light source.

[5] The endoscope system described in any one of [1] to [4], in which the light source control unit sets the light amount setting value according to an individual difference of at least one of the light sources.

[6] The endoscope system described in any one of [1] to [5], in which the endoscope is detachably connected to a light source device including the two or more light sources.

[7] The endoscope system described in any one of [1] to [6], in which the main wavelength of the light source is a centroid wavelength or a peak wavelength.

According to the invention, it is possible to maintain a constant light amount ratio for each wavelength of light emitted from the endoscope.

DESCRIPTION OF THE PREFERRED EMBODIMENTS

Hereinafter, the invention will be described in detail.

The description of component elements described below is made based on representative embodiments of the invention, but the invention is not limited to such embodiments.

The numerical range expressed by using "to" in this specification means a range including numerical values described before and after "to" as a lower limit and an upper limit.

In this specification, it is assumed that the terms "perpendicular" and "parallel" include the range of error accepted in the technical field to which the invention belongs. For example, "perpendicular" and "parallel" mean within a range of less than ±10° with respect to strictly perpendicular or parallel. The error with respect to strictly perpendicular or parallel is preferably 5° or less, more preferably 3° or less. In this specification, it is assumed that "same" includes an error range generally accepted in the technical field.

In this specification, it is assumed that the terms "all", "any one", "complete", and the like include not only a case of 100% but also the range of error generally accepted in the technical field. For example, a case of 99% or more, a case of 95% or more, or a case of 90% or more is included.

First Embodiment

Figure 1:
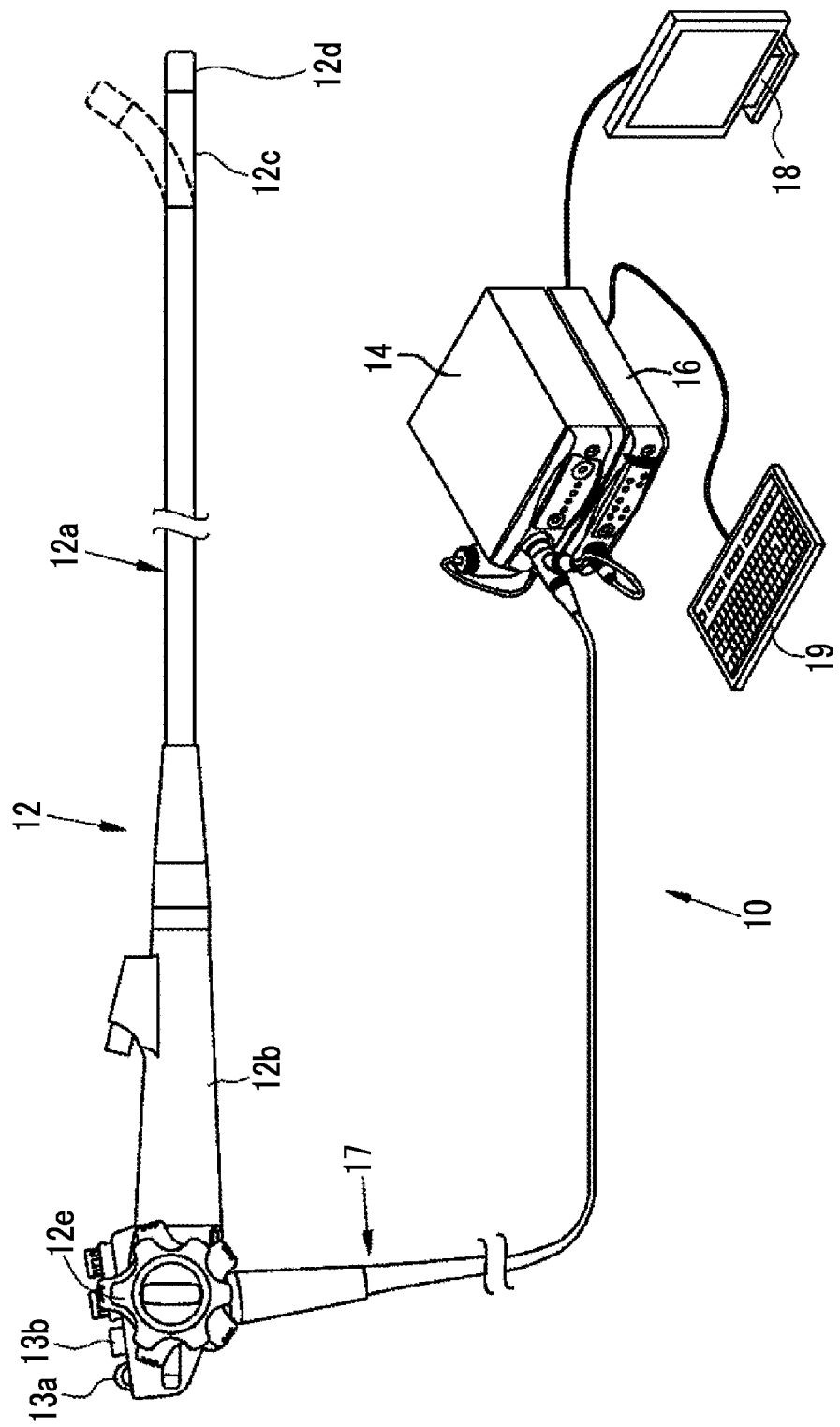
FIG. 1 is a perspective view conceptually showing an example of an endoscope system of the invention.
Figure 2:
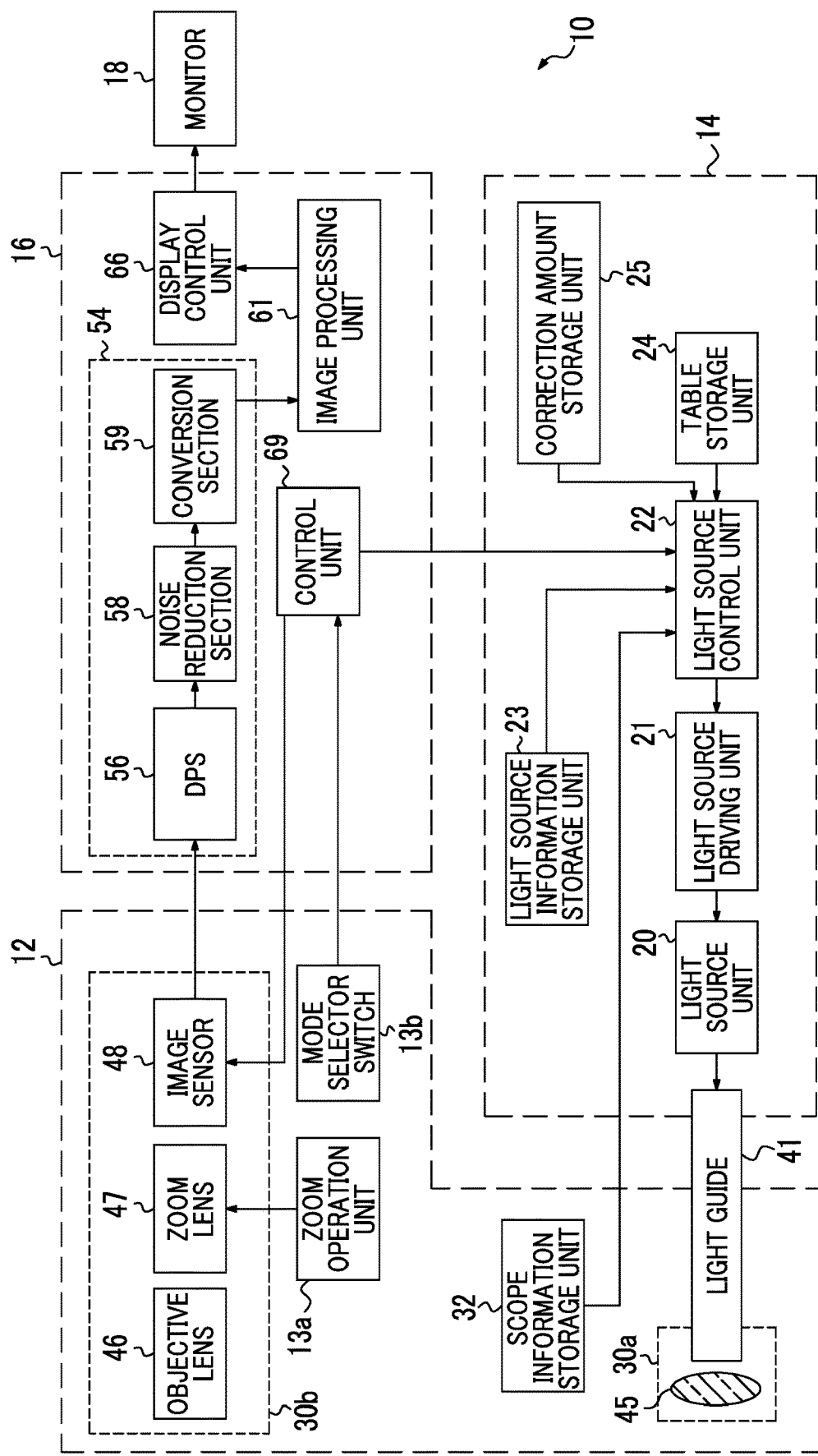
FIG. 2 is a block diagram of an example of the endoscope system of the invention.

FIG. 1 is a perspective view conceptually showing an example of a first embodiment of an endoscope system of the invention, and FIG. 2 is a block diagram of the endoscope system.

As shown in FIG. 1, an endoscope system 10 includes an endoscope 12 for imaging an observation part in a living body (in a subject), a processor device 16 for generating a display image of the observation part based on an image signal obtained by the imaging, a light source device for an endoscope (hereinafter, simply referred to as a light source device) 14 for supplying illumination light, which is to be emitted to the observation part, to the endoscope 12, and a monitor 18 for displaying the display image. An instruction input part (console) 19, such as a keyboard or a mouse, is connected to the processor device 16.

The endoscope system 10 can execute a normal observation mode for observing an observation part and a blood vessel emphasis observation mode for emphasizing and observing a blood vessel present inside the mucosa of an observation part. The blood vessel emphasis observation mode is a mode for performing diagnosis, such as determination regarding whether a tumor is benign or malignant, by visualizing a blood vessel pattern as blood vessel information. In the blood vessel emphasis observation mode, illumination light including a large amount of light components in a specific wavelength band having high absorbance for blood hemoglobin is emitted to the observation part.

In the normal observation mode, a normal observation image suitable for observation of the entire observation part is generated as a display image. In the blood vessel emphasis observation mode, a blood vessel emphasis observation image suitable for observation of a pattern of a blood vessel is generated as a display image.

The endoscope 12 has an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 12e of the operation unit 12b, the bending portion 12c is bent. As a result of the bending of the bending portion 12c, the distal end portion 12d faces in a desired direction. An injection port (not shown) for injecting air, water, or the like toward the observation target is provided in the distal end portion 12d. In addition to the angle knob 12e, a forceps port for inserting a treatment tool, an air and water supply button operated in the case of supplying air and water through an air and water supply nozzle, a freeze button (not shown) for capturing a still image, a zoom operation unit 13a, and a mode selector switch 13b are provided in the operation unit 12b. The zoom operation unit 13a is used in the case of enlarging or reducing the observation target. The mode selector switch 13b is used to switch the observation mode in a case where the endoscope system 10 has a plurality of observation modes.

The endoscope 12 includes a universal cord 17 for connecting the endoscope 12 to the processor device 16 and the light source device 14.

A communication cable or a light guide 41 extending from the insertion part 12a is inserted into the universal cord 17, and a connector is attached to one end of the universal cord 17 on a side of the processor device 16 and the light source device 14. The connector is a composite type connector including a communication connector and a light source connector. The communication connector and the light source connector are detachably connected to the processor device 16 and the light source device 14, respectively. One end of the communication cable is disposed in the communication connector. An incidence end of the light guide 41 is disposed in the light source connector.

The endoscope 12 has a scope information storage unit 32 that stores information of the type of the endoscope 12. The information of the type of the endoscope stored in the scope information storage unit 32 is supplied to a light source control unit 22 of the light source device 14 to which the endoscope 12 is connected.

As shown in FIG. 2, the light source device 14 includes: a light source unit 20 having two or more light sources having different main wavelengths; the light source control unit 22 for controlling the light emission timing, the light emission amount, and the like of the light source unit 20; a light source driving unit 21 that generates a driving current according to the control signal of the light source control unit 22 and supplies the driving current (driving signal) to each light source to emit light; a light source information storage unit 23 for storing information of the main wavelengths of two or more light sources included in the light source unit 20 of the light source device 14; a table storage unit 24 for storing at least information of the length of the light guide as a table for each type of the endoscope 12; and a correction amount storage unit 25 for storing a correction amount corresponding to the main wavelength of the light source and the length of the light guide as a table.

In the light source device 14, the light source control unit 22 acquires the information of the type of the endoscope from the scope information storage unit 32 of the connected endoscope 12, and acquires the information of the length of the light guide 41 of the endoscope 12 with reference to the table stored in the table storage unit 24. The light source control unit 22 sets a light amount setting value using the table stored in the correction amount storage unit 25 according to the acquired information of the length of the light guide 41 and the information of the main wavelength of the light source stored in the light source information storage unit 23, and inputs the light amount setting value to the light source driving unit 21 to control the light emission amount of the light source driven by the light source driving unit 21, thereby adjusting the light amount ratio in the light emitted from the endoscope 12.

This will be described in detail later.

The illumination light emitted from the light source unit 20 is incident on the light guide 41. The light guide 41 is built into the endoscope 12 and the universal cord 17, and propagates the illumination light to the distal end portion 12d of the endoscope 12. The universal cord 17 is a cord for connecting the endoscope 12 with the light source device 14 and the processor device 16. As the light guide 41, it is possible to use a multi-mode fiber. As an example, it is possible to use a small-diameter fiber cable having a diameter of $\phi 0.3$ mm to $\phi 0.5$ mm that includes a core with a diameter of 105 μm, a cladding with a diameter of 125 μm, and a protective layer as an outer skin.

An illumination optical system 30a and an imaging optical system 30b are provided in the distal end portion 12d of the endoscope 12. The illumination optical system 30a has an illumination lens 45, and illumination light is emitted to the observation target through the illumination lens 45. The imaging optical system 30b has an objective lens 46, a zoom lens 47, and an image sensor 48. The image sensor 48 images the observation target using reflected light (including scattered light, fluorescence emitted from the observation target, fluorescence due to medicine administered to the observation target, or the like in addition to the reflected light) of the illumination light that returns from the observation target through the objective lens 46 and the zoom lens 47. The zoom lens 47 is moved by operating the zoom operation unit 13a. As a result, the observation target to be imaged using the image sensor 48 is enlarged or reduced for observation.

In the present embodiment, the image sensor 48 photoelectrically converts the received light and accumulates the signal charge corresponding to the amount of received light for each pixel. The signal charge is converted into a voltage signal and read out from the image sensor 48. The voltage signal read out from the image sensor 48 is input to a DSP 56 as an image signal.

The image sensor 48 performs an accumulation operation of accumulating the signal charge in a pixel and a reading operation of reading the accumulated signal charge within the acquisition period of one frame. The light source device 14 generates illumination light according to the timing of the accumulation operation of the image sensor 48, and makes the illumination light incident on the light guide 41.

The image sensor 48 is a so-called primary color system color sensor having a color filter in each pixel. Accordingly, each pixel of the image sensor 48 has any one of an R color filter (red color filter), a G color filter (green color filter), and a B color filter (blue color filter), for example. A pixel having an R color filter is an R pixel, a pixel having a G color filter is a G pixel, and a pixel having a B color filter is a B pixel. Thus, the image sensor 48 has pixels of three colors of R pixel, G pixel, and B pixel. Accordingly, in the case of imaging the observation target using white light as illumination light, an R image obtained by imaging the observation target with the R pixel, a G image obtained by imaging the observation target with the G pixel, and a B image obtained by imaging the observation target with the B pixel are obtained at the same time.

As the image sensor 48, it is possible to use a charge coupled device (CCD) sensor or a complementary metal oxide semiconductor (CMOS) sensor. Although the image sensor 48 of the present embodiment is a primary color system color sensor, it is also possible to use a complementary color system color sensor. For example, the complementary color system color sensor includes a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors described above in the case of using the complementary color system color sensor can be converted into a B image, a G image, and an R image by performing complementary color-primary color conversion. Instead of the color sensor, a monochrome sensor in which no color filter is provided can be used as the image sensor 48. In this case, by sequentially imaging the observation target using the illumination light of respective colors, such as BGR, it is possible to obtain images of the respective colors described above.

A communication cable for communicating a driving signal for driving the image sensor 48 and an image signal output from the image sensor 48 or the light guide 41 for guiding the illumination light supplied from the light source device 14 to the illumination window is inserted into the insertion part 12*a*.

The processor device 16 has an image acquisition unit 54, an image processing unit 61, a display control unit 66, and a control unit 69.

The image acquisition unit 54 acquires captured images of a plurality of colors obtained by imaging the observation target using the image sensor 48. Specifically, the image acquisition unit 54 acquires a set of B image, G image, and R image for each imaging frame. The image acquisition unit 54 has a digital signal processor (DSP) 56, a noise reduction section 58, and a conversion section 59, and performs various kinds of processing on the acquired images using these.

The DSP 56 performs various kinds of processing, such as defect correction processing, offset processing, gain correction processing, linear matrix processing, gamma conversion processing, demosaic processing, and YC conversion processing, on the acquired images when necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting the signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing. The demosaic processing (also referred to as isotropic processing or simultaneous processing) is processing for interpolating the pixel values of missing pixels, and is applied to the image after the gamma conversion processing. The missing pixel is a pixel having no pixel value because pixels of other colors are arranged in the image sensor 48 for the arrangement of color filters. For example, since the B image is obtained by imaging the observation target in the B pixel, a pixel at a position corresponding to the G or R pixel of the image sensor 48 has no pixel value. The demosaic processing is for generating the pixel values of pixels at the positions of the G and R pixels of the image sensor 48 by interpolating the B image. The YC conversion processing is processing for converting the image after the demosaic processing into a brightness channel Y, a color difference channel Cb, and a color difference channel Cr.

The noise reduction section 58 performs noise reduction processing on the brightness channel Y, the color difference channel Cb, and the color difference channel Cr using, for example, a moving average method or a median filter method. The conversion section 59 reconverts the brightness channel Y, the color difference channel Cb, and the color difference channel Cr after the noise reduction processing into images of the respective colors of BGR.

The image processing unit 61 generates an observation image by performing color conversion processing, color emphasis processing, and structure emphasis processing on the B image, the G image, and the R image for one imaging frame subjected to the various kinds of processing described above. In the color conversion processing, 3×3 matrix processing, gradation conversion processing, three-dimensional look-up table (LUT) processing, and the like are performed on the images of the respective colors of BGR. The color emphasis processing is processing for emphasizing the color of the image, and the structure emphasis processing is processing for emphasizing the tissue or structure of the observation target, such as a blood vessel or a pit pattern, for example.

The display control unit 66 acquires observation images from the image processing unit 61 in a sequential manner, converts the acquired observation images into a format suitable for display, and sequentially outputs and displays the converted observation images on the monitor 18. As a result, a doctor or the like can observe the observation target using a still image or a motion picture of the observation image.

The control unit 69 is, for example, a central processing unit (CPU), and performs overall control of the endoscope system 10, such as synchronous control of the illumination light emission timing and the imaging frame. In a case where the endoscope system 10 has a plurality of observation modes, the control unit 69 switches the illumination light through the light source control unit 22 by receiving an instruction input from the mode selector switch 13*b*. As a result, the observation mode is switched.

The processor device 16 is electrically connected to the monitor 18 and the console 19. The monitor 18 outputs and displays an observation image, additional image information, and the like as necessary. The console 19 functions as a user interface for receiving an input operation, such as a function setting. In addition, an external recording unit (not shown) in which an image, image information, and the like are recorded may be connected to the processor device 16.

Figure 3:
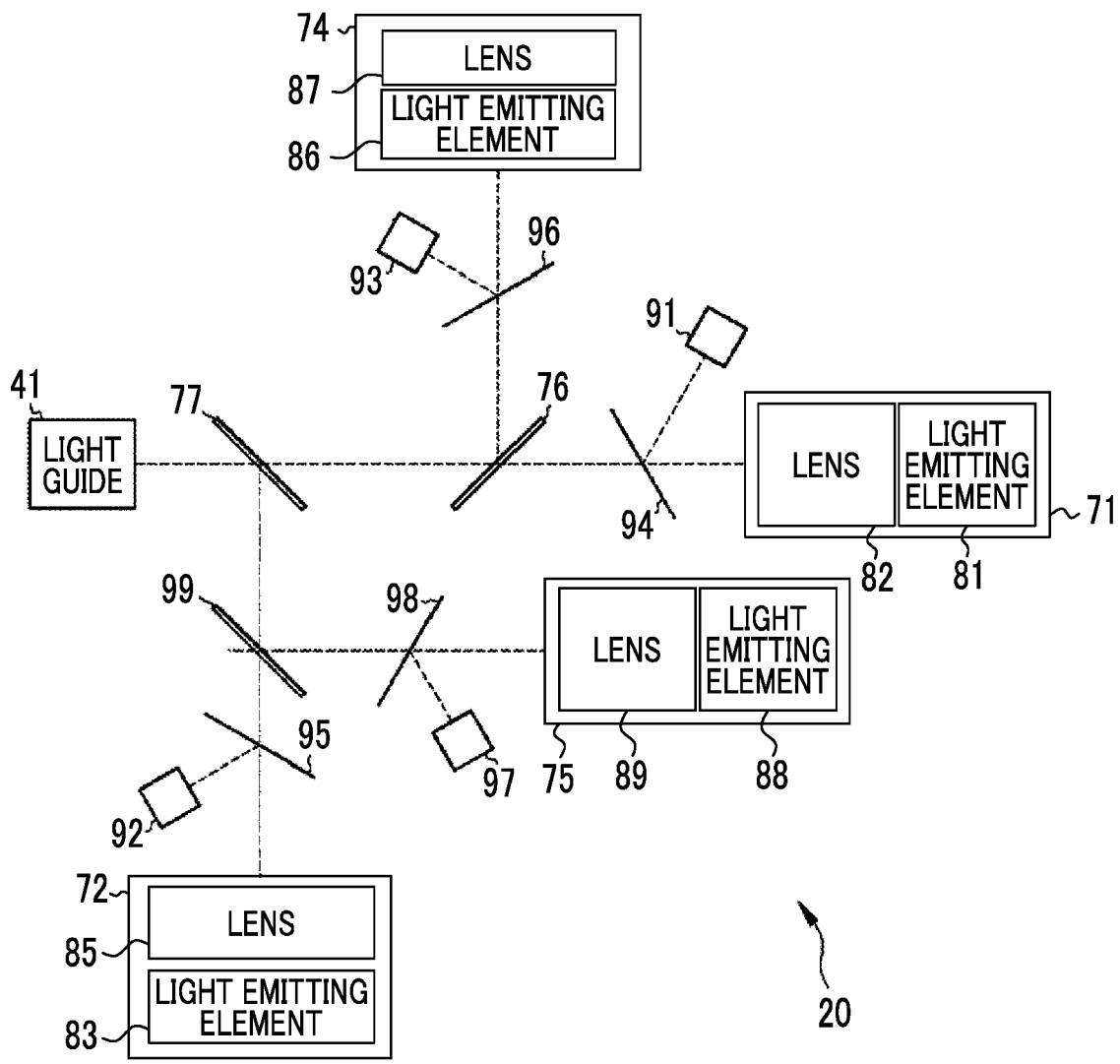
FIG. 3 is a block diagram of a light source unit.

Hereinafter, the configuration and operation of the light source device 14 will be described in more detail. As shown in FIG. 3, the light source unit 20 of the light source device 14 includes a first light source 71, a second light source 72, and a third light source 75. In the present embodiment, the light source unit 20 includes an additional light source 74 in addition to the first light source 71, the second light source 72, and the third light source 75. The first light source 71, the second light source 72, the third light source 75, and the additional light source 74 can be independently controlled.

In the normal observation mode, the light source control unit 22 turns on the first light source 71, the second light source 72, and the third light source 75, and turns off the additional light source 74. On the other hand, in the blood vessel emphasis observation mode, the light source control unit 22 turns on all of the first light source 71, the second light source 72, the third light source 75, and the additional light source 74.

In the normal observation mode, blue light emitted from the first light source 71, green light emitted from the second light source 72, and red light emitted from the third light source 75 are multiplexed to generate broadband white light. On the other hand, in the blood vessel emphasis observation mode, mixed light is generated by mixing white light with violet light having high absorbance for blood hemoglobin. In the blood vessel emphasis observation mode, the light source control unit 22 lowers the proportion of the amount of blue light so that the violet light is more dominant than the blue light.

The first light source 71 emits light of a blue component B (hereinafter, referred to as blue light). The first light source 71 includes a light emitting element 81 and a lens 82 for adjusting blue light emitted from the light emitting element 81 into parallel light or the like. The light emitting element 81 is, for example, a semiconductor element, such as a light emitting diode (LED) or a laser diode (LD). The blue light emitted from the first light source 71 is incident on the light guide 41 through multiplexing members 76 and 77 that transmit blue light. The multiplexing members 76 and 77 are, for example, dichroic mirrors or dichroic prisms.

In general, the wavelength of blue is about 445 nm to about 485 nm. For example, there is a case where a color intermediate between blue and green is referred to as blue green so as to be distinguished from blue. In the endoscope system 10, however, it is not necessary to excessively subdivide the type of color (name of color) at least for light emitted from each light source of the light source unit 20. Therefore, in this specification, the color of light having a wavelength of about 440 nm or more and less than about 490 nm is referred to as blue color. In addition, the color of light having a wavelength of about 490 nm or more and less than about 600 nm is referred to as green, and the color of light having a wavelength equal to or greater than about 600 nm and less than about 680 nm is referred to as red. The color of visible light having a wavelength less than "about 440 nm" that is the lower limit of the blue wavelength (for example, visible light having a wavelength equal to or greater than about 380 nm and less than about 440 nm) is referred to as violet, and the color of light which has a shorter wavelength than violet and for which the image sensor 48 has sensitivity is referred to as ultraviolet. The color of light which has a wavelength of "about 680 nm", which is the upper limit of the red wavelength, or more and for which the image sensor 48 has sensitivity is referred to as infrared. In this specification, "broadband" means that the wavelength range extends over a plurality of color wavelength ranges. White refers to the color of light including at least light belonging to the blue or violet color, light belonging to the green color, and light belonging to the red color.

The second light source 72 emits light of a green component G (hereinafter, referred to as green light). The second light source 72 includes a light emitting element 83 and a lens 85 for adjusting green light emitted from the light emitting element 83 into parallel light or the like. The light emitting element 83 is, for example, a semiconductor element, such as an LED or an LD. The green light emitted from the second light source 72 is incident on the light guide 41 through multiplexing members 99 and 77 that transmit green light. The multiplexing member 99 is, for example, a dichroic mirror or a dichroic prism.

The third light source 75 emits light of a red component R (hereinafter, referred to as red light). The third light source 75 includes a light emitting element 88 and a lens 89 for adjusting red light emitted from the light emitting element 88 into parallel light or the like. The light emitting element 88 is, for example, a semiconductor element, such as an LED or an LD. The red light emitted from the third light source 75 is incident on the light guide 41 through the multiplexing members 99 and 77 that transmit red light.

The additional light source 74 emits light including a violet component V (hereinafter, referred to as violet light). The additional light source 74 includes a light emitting element 86 and a lens 87 for adjusting violet light emitted from the light emitting element 86 into parallel light or the like. The light emitting element 86 is, for example, a semiconductor element, such as an LED or an LD. The violet light emitted from the additional light source 74 is incident on the light guide 41 through the multiplexing member 76 that reflects violet light and the multiplexing member 77 that transmits violet light. The violet component V of violet light is received by the B pixel in the image sensor 48. For this reason, the reflected light of violet light and the like contribute to the B image together with the reflected light of blue light and the like.

In addition to the first light source 71, the second light source 72, the third light source 75, and the additional light source 74, the light source unit 20 includes photodetectors 91, 92, 93, and 97, beam splitters 94, 95, 96, and 98, and a cooling member (so-called heat sink; not shown) for cooling the light emitting element of each light source. The beam splitter 94 reflects a part of blue light emitted from the first light source 71 at a predetermined ratio, and the photodetector 91 receives the blue light reflected by the beam splitter 94. The beam splitter 95 reflects a part of green light emitted from the second light source 72 at a predetermined ratio, and the photodetector 92 receives the green light reflected by the beam splitter 94. The beam splitter 98 reflects a part of red light emitted from the third light source 75 at a predetermined ratio, and the photodetector 97 receives the red light reflected by the beam splitter 98. The beam splitter 96 reflects a part of violet light emitted from the additional light source 74 at a predetermined ratio, and the photodetector 93 receives the violet light reflected by the beam splitter 96. The light source control unit 22 controls the light emission amount of the blue light of the first light source 71 automatically and accurately using the light amount detected by the photodetector 91. In addition, the light source control unit 22 controls the light emission amount of the green light of the second light source 72 automatically and accurately using the light amount detected by the photodetector 92. In addition, the light source control unit 22 controls the light emission amount of the red light of the third light source 75 automatically and accurately using the light amount detected by the photodetector 97. Similarly, the light source control unit 22 controls the light emission amount of the violet light of the additional light source 74 automatically and accurately using the light amount detected by the photodetector 93.

Figure 4:
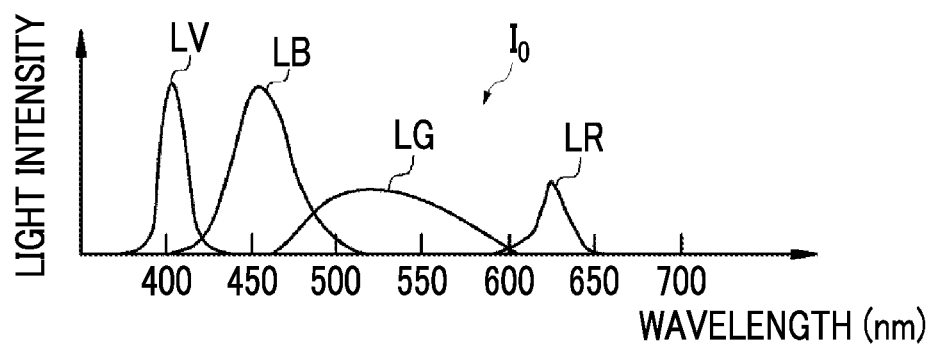
FIG. 4 is a graph schematically showing the intensity spectra of red light, green light, blue light, and violet light.

The light source device 14 configured as described above emits light so that light, which is emitted from the light source device 14, passes through the light guide 41 of the endoscope 12, and is emitted from the distal end portion 12d of the endoscope, becomes almost white illumination light, for example, illumination light $I_0$ shown in FIG. 4. Then, the image sensor 48 images an observation target using the illumination light including the blue light, the green light, and the red light emitted from the light source device 14.

That is, in FIG. 4, a blue component LB included in the illumination light $I_0$ is the blue component LB of blue light that is emitted from the first light source 71 and is guided through the light guide 41 to be attenuated. A green component LG included in the illumination light $I_0$ is the green component LG of green light that is emitted from the second light source 72 and is guided through the light guide 41 to be attenuated. A red component LR included in the illumination light $I_0$ is the red component LR of red light that is emitted from the third light source 75 and is guided through the light guide 41 to be attenuated. A violet component LV included in the illumination light $I_0$ is the violet component LV of violet light that is emitted from the additional light source 74 and is guided through the light guide 41 to be attenuated.

As described above, in the light source device 14, the light source control unit 22 acquires the information of the type of the endoscope from the scope information storage unit 32 of the connected endoscope 12, and acquires the information of the length of the light guide 41 of the endoscope 12 with reference to the table stored in the table storage unit 24. The light source control unit 22 sets a light amount setting value using the table stored in the correction amount storage unit 25 according to the acquired information of the length of the light guide 41 and the information of the main wavelength of the light source stored in the light source information storage unit 23, and inputs the light amount setting value to the light source driving unit 21 to control the light emission amount of the light source driven by the light source driving unit 21, thereby adjusting the light amount ratio in the light emitted from the endoscope 12 to a preset light amount ratio.

The correction amount storage unit 25 stores light amount setting values corresponding to a combination of the lengths of a plurality of light guides and the main wavelength of the light source, which are calculated in advance by performing test or the like, as a table.

In addition, the table storage unit 24 stores information, such as the length of the light guide 41, in advance as a table for each type of the endoscope.

Figure 5:
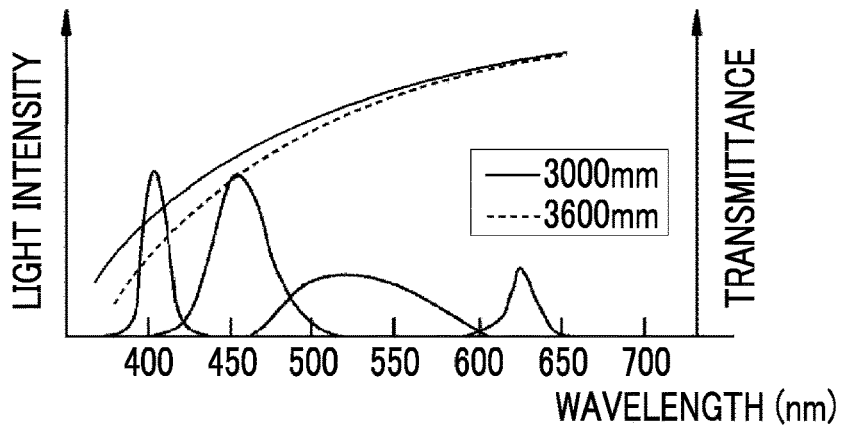
FIG. 5 is a graph showing the relationship between the wavelength and the light intensity and the transmittance.

FIG. 5 conceptually shows the relationship between the wavelength and the transmittance in a case where the length of the light guide 41 is 3000 mm and a case where the length of the light guide 41 is 3600 mm. As shown in FIG. 5, the larger the length of the light guide 41, the lower the transmittance. In this case, on the short wavelength side, a reduction in the transmittance is larger than that on the long wavelength side.

Therefore, assuming that the light emission amount of each light source is the same in the case where the length of the light guide 41 is 3000 mm and the case where the length of the light guide 41 is 3600 mm, the light amount ratio of the light emitted from the endoscope 12, that is, the proportion of each component is different between the case of 3000 mm and the case of 3600 mm. That is, in the case where the length of the light guide 41 is 3000 mm and the case where the length of the light guide 41 is 3600 mm, the color of the light emitted from the endoscope 12 changes.

In the invention, therefore, for example, even in a case where the endoscope 12 having the light guides 41 having different lengths is connected to the light source device 14 with the case where the length of the light guide 41 is 3000 mm as a reference, the light emission amounts of the first light source 71, the second light source 72, the third light source 75, and the additional light source 74 are adjusted so that the light amount ratio in the light emitted from the endoscope 12 in the case of the reference length is the same.

For example, with the case where the length of the light guide 41 is 3000 mm as a reference, the light emission amount of each light source at which the light emitted from the endoscope 12 has a desired color (for example, white light) in the case where the length is 3000 mm is set as the reference of the light emission amount of each light source.

In a case where the endoscope 12 having the light guide 41 having a length of 3600 mm is connected to the light source device 14, the light source control unit 22 acquires the information of the type of the endoscope from the scope information storage unit 32, and acquires the information of the length of the light guide 41 from the information of the type of the endoscope by referring to the table stored in the table storage unit 24. In addition, the light source control unit 22 acquires the information of the main wavelength of each light source (the first light source 71, the second light source 72, the third light source 75, and the additional light source 74) from the light source information storage unit 23.

From the information of the length of the light guide 41 and the information of the main wavelength of each light source, the light source control unit 22 sets a light amount setting value for each light source using the table stored in the correction amount storage unit 25. In this case, the light amount setting value is set such that the ratio of the light emission amount of a light source, which emits light on the shorter wavelength side, to the light emission amount in a case where the length of the light guide 41 is a reference length becomes larger. That is, the ratio of the light emission amount of each light source to the reference light emission amount in a case where the endoscope 12 having the light guide 41 having a length of 3600 mm is connected increases in order of the third light source 75, the second light source 72, the first light source 71, and the additional light source 74.

By changing the light emission amounts of the first light source 71, the second light source 72, the third light source 75, and the additional light source 74 according to the main wavelength of each light source and the length of the light guide 41, even in a case where the endoscope 12 having the light guide 41 having a length of 3600 mm is connected, the light amount ratio in the light emitted from the endoscope 12 can be made to be equal to the light amount ratio of the light emitted from the endoscope 12 in the case of the reference (the length of the light guide 41 is 3000 mm).

By changing the light emission amount of each light source according to the main wavelength of each light source and the length of the light guide 41 as described above, it is possible to maintain a constant light amount ratio for each wavelength of the light emitted from the endoscope 12.

In the first embodiment described above, all of the four light sources are configured such that the light emission amount is set according to the information of the main wavelength of the light source and the information of the length of the light guide 41. However, the invention is not limited thereto, and the light emission amount may be set according to the information of the main wavelength of the light source and the information of the length of the light guide 41 for at least one light source.

As described above, since the influence on the change in the length of the light guide 41 becomes larger as the wavelength becomes shorter, it is preferable to set the light emission amount of the light source, which emits light on the short wavelength side, according to the information of the main wavelength of the light source and the information of the length of the light guide 41. For example, in the example shown in FIG. 3, for the first light source that emits blue light and/or the additional light source that emits violet light, it is preferable to set the light emission amount according to the information of the main wavelength of the light source and the information of the length of the light guide 41.

In the first embodiment described above, four light sources having different main wavelengths are provided. However, the invention is not limited thereto, and two or three light sources having different main wavelengths may be provided, or five or more light sources having different main wavelengths may be provided. Alternatively, regardless of the number of light sources, for at least one light source, the light emission amount may be set according to the information of the main wavelength of the light source and the information of the length of the light guide 41.

As described above, the influence on the change in the length of the light guide 41 becomes larger as the wavelength becomes shorter. Therefore, in a case where at least one of two or more light sources is a blue light source that emits blue light, it is preferable to set the light emission amount of the blue light source according to the information of the main wavelength of the light source and the information of the length of the light guide 41.

Here, the main wavelength of the light source is a centroid wavelength or a peak wavelength. The centroid wavelength is an average wavelength of the spectrum of light emitted from the light source. The peak wavelength is a wavelength showing the maximum value in the spectrum of light emitted from the light source.

In the first embodiment described above, for at least one light source, the light emission amount is set according to the information of the main wavelength of the light source and the information of the length of the light guide 41. However, the invention is not limited thereto.

For example, the type of the illumination lens 45 may differ depending on the type of the endoscope 12. The transmittance of the illumination lens 45 also differs depending on its type, but the rate of change in transmittance may differ depending on the wavelength. Therefore, the light emission amount of the light source may be set according to the information of the illumination lens 45 as well as the information of the main wavelength of the light source and the information of the length of the light guide 41.

In this case, the table storage unit 24 stores the information of the length of the light guide 41 and the information of the illumination lens 45 as a table for each type of the endoscope 12. The light source control unit 22 acquires the information of the length of the light guide 41 of the endoscope 12 and the information of the illumination lens 45 from the information of the endoscope acquired from the scope information storage unit 32 by referring to the table stored in the table storage unit 24.

Alternatively, the transmittance changes depending on the material and thickness of the light guide 41, the number of fiber cables, and the like. Therefore, the light emission amount of the light source may be set according to the information of the type of the light guide 41 as well as the information of the main wavelength of the light source and the information of the length of the light guide 41.

In this case, the table storage unit 24 stores the information of the length of the light guide 41 and the information of the type (for example, a material, a thickness, and the number of fiber cables) of the light guide 41 as a table for each type of the endoscope 12. The light source control unit 22 acquires the information of the length of the light guide 41 of the endoscope 12 and the information of the type of the light guide 41 from the information of the endoscope acquired from the scope information storage unit 32 by referring to the table stored in the table storage unit 24.

The light emission amount of the light source may be set according to the information of the main wavelength of the light source, the information of the length of the light guide 41, the information of the illumination lens 45, and the information of the type of the light guide 41.

In the first embodiment described above, the endoscope 12 has the scope information storage unit 32 that stores the information of the type of the endoscope, and the light source control unit 22 acquires the information of the length of the light guide 41 (and the information of the illumination lens 45 and the information of the type of light guide 41) from the information of the type of the endoscope acquired from the scope information storage unit 32 by referring to the table stored in the table storage unit 24. However, the invention is not limited thereto, and the endoscope 12 may have a storage unit that stores the information of the length of the light guide 41 (and the information of the illumination lens 45 and the information of the type of light guide 41), and the light source control unit 22 may acquire the information of the length of the light guide 41 directly from the storage unit.

The information of the main wavelength of each light source stored in the light source information storage unit 23 may be a main wavelength on the specification of the light source. In practice, however, there are individual differences even in the case of light sources of the same type. For this reason, the wavelength of emitted light has a variation of about ±5 nm with respect to the specification wavelength. Therefore, it is preferable that the light source information storage unit 23 stores the main wavelength obtained by actually measuring the spectrum of light emitted from each light source.

Figure 6:
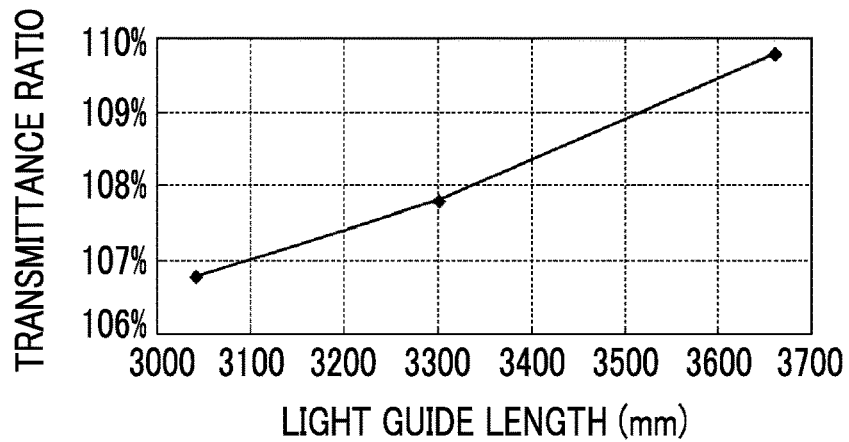
FIG. 6 is a graph showing the relationship between the length of a light guide and the transmittance ratio.

FIG. 6 shows the relationship between the transmittance ratio and the length of the light guide in the case of a wavelength of 405 nm and the case of a wavelength of 409 nm.

As can be seen from FIG. 6, even in a case where the wavelength difference is small as in the case of the wavelength of 405 nm and the case of the wavelength of 409 nm, the transmittance ratio changes greatly as the length of the light guide changes. That is, even in the case of light sources of the same type, the transmittance changes depending on the individual difference.

Therefore, by configuring the light source information storage unit 23 so as to store the main wavelength obtained by actually measuring the spectrum of light emitted from each light source, the light source control unit 22 can set the light amount setting value according to the individual difference of the light source by setting the light amount setting value according to the main wavelength.

In the first embodiment described above, one light source driving unit 21 is configured to supply the driving signal to each of the four light sources to emit light. However, the invention is not limited thereto, and four light source driving units corresponding to the respective light sources may be provided.

Second Embodiment

In the first embodiment described above, each of the four light sources is configured to mainly emit light of one color component. However, the invention is not limited thereto, and a light source that emits light of two or more color components may be used.

Figure 7:
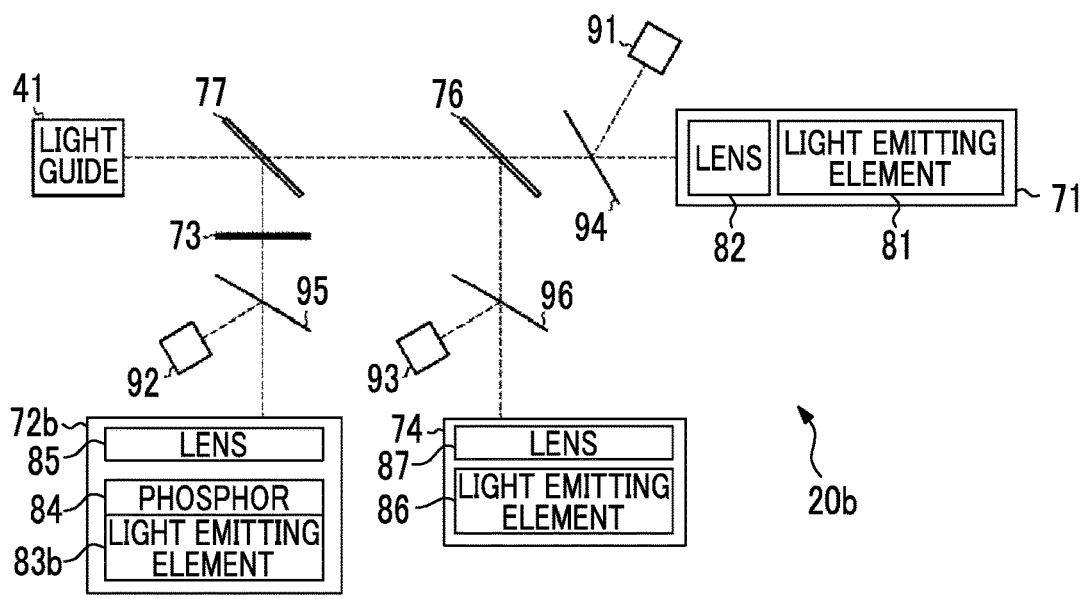
FIG. 7 is a block diagram of another example of the light source unit.

FIG. 7 shows a block diagram of another example of a light source unit. Since the endoscope system of the second embodiment has the same configuration as the endoscope system of the first embodiment except for the configuration of a light source unit, only the configuration of the light source unit will be described below.

A light source unit 20b shown in FIG. 7 includes a first light source 71, a second light source 72b, and an optical filter 73. In the present embodiment, the light source unit 20b includes an additional light source 74 in addition to the first light source 71 and the second light source 72b. The first light source 71, the second light source 72b, and the additional light source 74 can be independently controlled.

The first light source 71 emits light of a blue component B (hereinafter, referred to as blue light). The first light source 71 includes a light emitting element 81 and a lens 82 for adjusting blue light emitted from the light emitting element 81 into parallel light or the like. The light emitting element 81 is, for example, a semiconductor element, such as an LED or an LD. The blue light emitted from the first light source 71 is incident on the light guide 41 through multiplexing members 76 and 77 that transmit blue light. The multiplexing members 76 and 77 are, for example, dichroic mirrors or dichroic prisms.

The second light source 72b emits broadband light including a red component R in addition to a green component G. However, since light emitted from the second light source 72b has a greater amount of green component G than the amount of red component R, the light emitted from the second light source 72b is usually green if viewed. In this specification, therefore, the light emitted from the second light source 72b is referred to as green light. That is, the second light source 72b is a light source that emits broadband green light.

Figure 8:
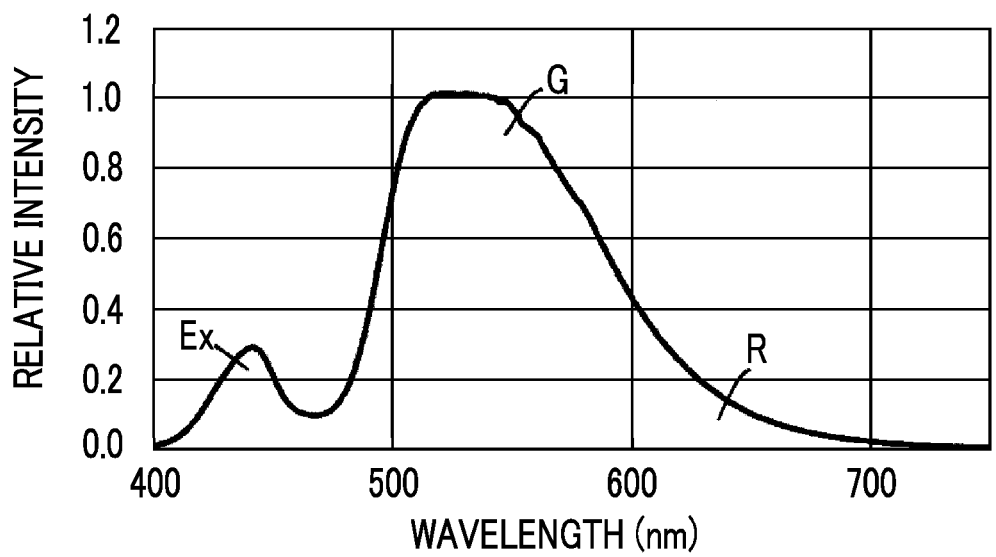
FIG. 8 is a graph showing the relationship between the wavelength and the relative intensity.

The second light source 72b includes a light emitting element 83b that emits excitation light Ex, a phosphor 84 that emits green light in a case where the excitation light Ex emitted from the light emitting element 83b is incident thereon, and a lens 85 for arranging the broadband green light emitted from the phosphor 84 into parallel light or the like. The light emitting element 83 is, for example, a semiconductor element, such as an LED or an LD. As shown in FIG. 8, the excitation light Ex is blue light having a peak at about 445 nm, and the green light emitted from the phosphor 84 is broadband green light including the red component R in addition to the green component G. The broadband green light emitted from the second light source 72b as described above is incident on the light guide 41 through the optical filter 73 and the multiplexing member 77 that reflects the green component G and the red component R.

Figure 9:
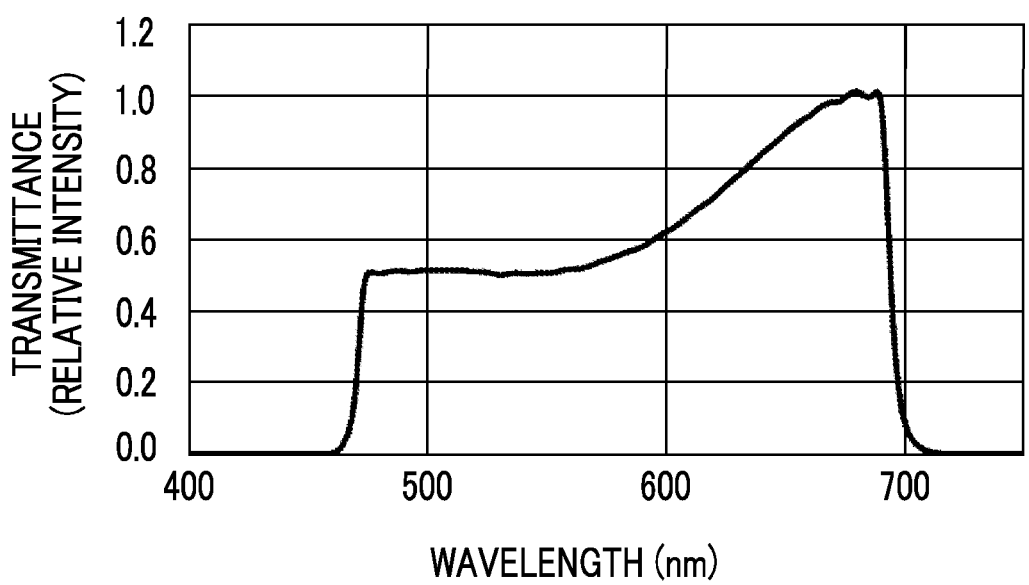
FIG. 9 is a graph showing the relationship between the wavelength and the transmittance.
Figure 10:
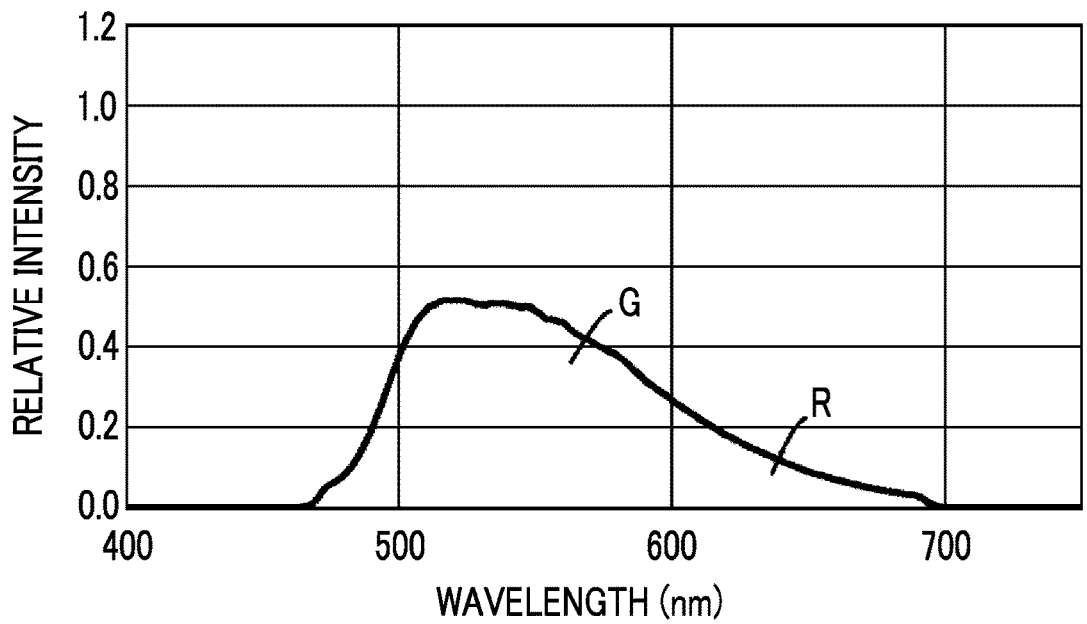
FIG. 10 is a graph showing the relationship between the wavelength and the relative intensity.

The optical filter 73 has a spectral transmittance shown in FIG. 9. Therefore, as shown in FIG. 10, the optical filter 73 adjusts the amount of broadband green light, which is emitted from the second light source 72b, for each wavelength. More specifically, the optical filter 73 adjusts the light amount ratio R/G between the green component G and the red component R of the broadband green light emitted from the second light source 72b.

For example, in the present embodiment, the light amount ratio R/G between the green component G and the red component R of the broadband green light emitted from the second light source 72b is about 0.15. On the other hand, due to the optical filter 73, the light amount ratio R/G between the green component G and the red component R of the broadband green light becomes about 0.22 when the broadband green light is incident on the light guide 41. In a case where the light amount of the green component G of the broadband green light emitted from the second light source 72b (that is, before passing through the optical filter 73) is set to "Gb" and the amount of green light after passing through the optical filter 73 is set to "Ga", the light amount ratio Ga/Gb between the green component G before passing through the optical filter 73 and the green component G after passing through the optical filter 73 is about 0.52. In a case where the light amount of the red component R of the broadband green light emitted from the second light source 72b is set to "Rb" and the amount of green light after passing through the optical filter 73 is set to "Ra", the light amount ratio Ra/Rb between the red component R before passing through the optical filter 73 and the red component R after passing through the optical filter 73 is about 0.75.

As described above, the reason why the optical filter 73 adjusts the light amount ratio R/G between the green component G and the red component R of the broadband green light is to convert the illumination light into white light suitable for imaging the observation target. The white light suitable for imaging the observation target is, for example, white light used as illumination light in a known endoscope system. The light source device 14 of the endoscope system 10 includes the first light source 71 that emits blue light and the second light source 72b that emits broadband green light, but does not have a light source that emits red light. Therefore, although the red component R is included in the broadband green light, if the blue light and the broadband green light are simply combined to form illumination light, the red component R is insufficient relative to the blue component B and the green component G in the illumination light after the combination. For this reason, the illumination light after the combination becomes, for example, cyan (light blue). As a result, the color of the observation image becomes unnatural.

On the other hand, by adjusting the light amount ratio R/G between the green component G and the red component R of the broadband green light as described above using the optical filter 73, the light amount ratio between at least the green component G and the red component R included in the illumination light becomes a light amount ratio suitable for imaging the observation target. The amount of blue light of the first light source 71 and the amount of broadband green light of the second light source 72b can be independently controlled. Therefore, by adjusting the light amount ratio R/G between the green component G and the red component R of the broadband green light as described above using the optical filter 73 and appropriately adjusting the light emission amounts of the first light source 71 and the second light source 72b according to the information of the length of the light guide 41 and the information of the main wavelength of the light source using the light source control unit 22, the illumination light becomes white light suitable for imaging the observation target.

A specific adjustment target value of the light amount ratio R/G is determined in consideration of the spectral characteristics of the broadband green light emitted from the second light source 72b, the spectral characteristics of the color filter of each color of the image sensor 48, a gain when acquiring an image from the image sensor 48, the content of various kinds of processing (for example, a matrix used in linear matrix processing) performed by the DSP 56, and the like. As a result, the optical filter 73 adjusts a brightness ratio between the G image and the R image. Therefore, when the light amount ratio between the green component G and the red component R of the broadband green light is adjusted using the optical filter 73, a brightness ratio between the G image and the R image obtained in the case of imaging the observation target using white light as an adjustment target becomes almost equal to a brightness ratio between the G image and the R image obtained in the case of imaging the observation target using the illumination light generated by the light source device 14. That is, the light source device 14 does not have a red light source that emits red light, but the obtained observation image has the same color tone as an observation image obtained in the case of imaging the observation target using the white light as an adjustment target.

Since the illumination light is converted into white light using the red component R, which is a part on the long wavelength side of the broadband green light of the second light source 72b, instead of providing a red light source for emitting red light in the light source unit 20 as described above, the amount of green component G becomes larger than the amount of red component R. Therefore, for the spectral transmittance of the optical filter 73, at least the transmittance of the green component G is lower than the transmittance of the red component R. In the present embodiment, the optical filter 73 transmits the broadband green light emitted from the second light source 72b and guides the broadband green light to the light guide 41. However, it is needless to say that the optical filter 73 can reflect the broadband green light and guide the broadband green light to the light guide 41. In this case, the spectral reflectance of the optical filter 73 is the same as, for example, that in FIG. 9, and at least the reflectance of the green component is lower than the reflectance of the red component. That is, the optical filter 73 has a characteristic (spectral reflectance) in which at least the reflectance of the green component G is lower than the reflectance of the red component R in the case of reflecting the broadband green light and guiding the broadband green light to the light guide 41, or has a characteristic (spectral transmittance) in which at least the transmittance of the green component G is lower than the transmittance of the red component R in the case of transmitting the broadband green light and guiding the broadband green light to the light guide 41.

Figure 11:
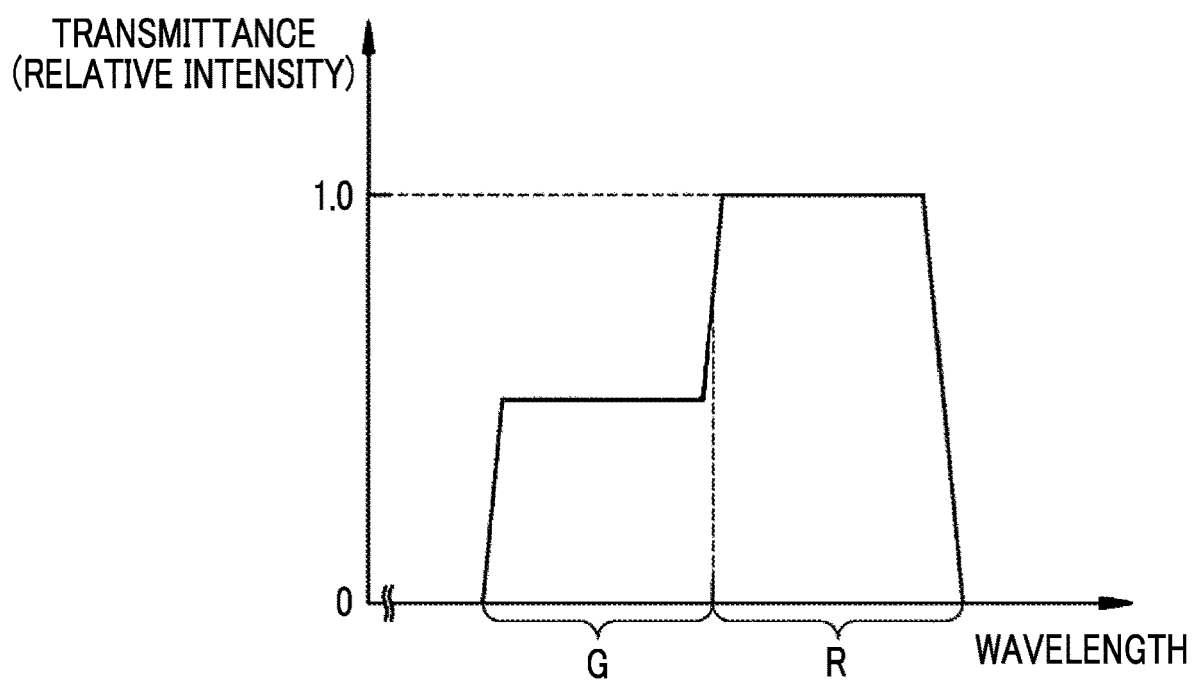
FIG. 11 is a graph showing the relationship between the wavelength and the transmittance.

The optical filter 73 has a transmittance for each wavelength that changes smoothly. Specifically, in the range of the green component G, the transmittance for each wavelength is substantially constant. In the range of the red component R, the transmittance for each wavelength gradually rises smoothly toward the long wavelength side. The spectral transmittance is determined in consideration of the reproducibility (ease of viewing) of a structure, such as a blood vessel. For example, in the endoscope system 10 and a known endoscope system, the depth or thickness of a blood vessel that is easily viewed changes according to the wavelength of light included in the illumination light. For this reason, if the spectral spectrum (light amount for each wavelength) of the illumination light is different, a blood vessel at certain depth and thickness may differ in ease of viewing. Therefore, the optical filter 73 smoothly changes the reflectance for each wavelength, and approximately reproduces almost the same spectral spectrum as the white light as an adjustment target in the range of the green component G and the red component R. In the case of configuring the optical filter 73 more easily, it is possible to make the change in transmittance for each wavelength stepwise. For example, as shown in FIG. 11, it is possible to adopt a configuration in which the spectral transmittance of the optical filter 73 is substantially constant in the wavelength range of the green component G and the wavelength range of the red component R. The spectral reflectance of the optical filter 73 in the case of reflecting broadband green light and guiding the broadband green light to the light guide 41 is also the same.

As can be seen from the spectral transmittance (see FIG. 9), the optical filter 73 also functions as an excitation light cut filter that cuts the excitation light Ex. Accordingly, a part of the excitation light Ex passes through the phosphor 84 and is then incident on the optical filter 73, but is not incident on the light guide 41 since it is cut by the optical filter 73. Although the optical filter 73 and the multiplexing member 77 are separately provided in the present embodiment, the optical filter 73 and the multiplexing member 77 can be integrated. In this case, the optical filter 73 adjusts the light amount ratio between the green component G and the red component R when the broadband green light is reflected to be guided to the light guide 41, and also functions as a multiplexing member that combines the blue light or the like emitted from the first light source 71 with the broadband green light emitted from the second light source 72b.

The light source device 14 having the light source unit 20b configured as described above emits substantially white illumination light. Then, the image sensor 48 images an observation target using illumination light including the blue light emitted from the light source unit 20b and the broadband green light whose components have been adjusted by the optical filter 73.

In the endoscope system, the DSP 56, the noise reduction section 58, the conversion section 59, the image processing unit 61, the display control unit 66, the control unit 69, the light source control unit 22, and the like are formed by using a CPU and an operation program for making the CPU perform various kinds of processing. In the invention, however, these parts may be formed by digital circuits.

Next, the operation of the endoscope system 10 will be described. In the case of performing endoscopic diagnosis, the endoscope 12 is connected to the processor device 16 and the light source device 14, and the processor device 16 and the light source device 14 are turned on to start the endoscope system 10.

The insertion part 12a of the endoscope 12 is inserted into the gastrointestinal tract of the subject, and the observation of the inside of the digestive tract is started. In the normal observation mode, the first light source 71, the second light source 72, and the third light source 75 excluding the additional light source 74 are turned on at the same time. Blue light, green light, and red light are emitted from the first light source 71, the second light source 72, and the third light source 75, respectively. The emitted blue light, green light, and red light are multiplexed in the light source unit 20 to generate white light. The white light is supplied to the light guide 41 of the endoscope 12.

In the endoscope 12, the white light is guided to the distal end portion 12d of the endoscope 12 through the light guide 41, and is emitted to the observation part from the distal end portion 12d. Reflected light of the white light reflected at the observation part is incident on the image sensor 48 from the observation window. The image sensor 48 photoelectrically converts the reflected light to generate an image signal. This image signal is input to the DSP 56 of the processor device 16. The image signal input to the DSP 56 may be obtained by performing processing, such as analog-to-digital conversion (A/D conversion), in the endoscope 12.

The DSP 56 obtains image data by performing signal processing, such as pixel interpolation processing, gamma correction, and white balance correction, on the image signal input from the endoscope 12 in units of a frame, and stores the image data in a frame memory. The image processing unit 61 performs predetermined image processing on the image data stored in the frame memory to generate a normal observation image. The normal observation image is displayed on the monitor 18 through the display control unit 66. The normal observation image is updated according to the frame rate of an image sensor 48.

The DSP 56 calculates the brightness (average brightness value) of the observation part based on the image signal inputted from the endoscope 12, and inputs the brightness to the control unit 69. The control unit 69 generates a light modulation signal, which is a difference between the input average brightness value and the target value, and inputs the light modulation signal to the light source control unit 22 of the light source device 14.

The light source control unit 22 adjusts the light amount setting value based on the light modulation signal and inputs the adjusted light amount setting value to the light source driving unit 21. In the normal observation mode, a light amount setting value for setting the light emission amounts of the first light source 71, the second light source 72, and the third light source 75 is input from the light source control unit 22 to the light source driving unit 21.

In this case, the light source control unit 22 acquires the information of the type of the endoscope from the scope information storage unit 32 of the connected endoscope 12, and acquires the information of the length of the light guide 41 of the endoscope 12 with reference to the table stored in the table storage unit 24. According to the acquired information of the length of the light guide 41 and the information of the main wavelength of the light source stored in the light source information storage unit 23, the light source control unit 22 sets a light amount setting value for each light source using the table stored in the correction amount storage unit 25.

The light source control unit 22 adjusts the light amount ratio in the light emitted from the endoscope 12 to the preset light amount ratio by controlling the light emission amount of each light source driven by the light source driving unit 21. As a result, even in a case where any endoscope 12 is used, the ratio of the amounts of red light, green light, and blue light in the illumination light emitted from the endoscope 12 is maintained constant, and a change in the color of the normal observation image is prevented.

Next, in a case where an observation part suspected as a lesion is found in the normal observation mode, the normal observation mode is switched to the blood vessel emphasis observation mode. In the blood vessel emphasis observation mode, the first light source 71, the second light source 72, the third light source 75, and the additional light source 74 are turned on at the same time. In this case, in the light source unit 20, mixed light in which violet light is mixed with white light is generated and supplied to the light guide 41 of the endoscope 12.

In the endoscope 12, reflected light of the mixed light emitted to the observation part is imaged similarly to the case of the normal observation mode, and the image signal is input to the processor device 16. In the processor device 16, the same operation as in the normal observation mode is performed except that the image processing unit 61 generates a blood vessel emphasis observation image and the display control unit 66 displays the blood vessel emphasis observation image on the monitor 18.

In addition to the light amount setting value for the first light source 71, the second light source 72, and the third light source 75, the light amount setting value for setting the light emission amount of the additional light source 74 is input from the light source control unit 22 to the light source driving unit 21 in the light source device 14. This is the same as in the normal observation mode except that the light source control unit 22 sets the light amount setting value for the additional light source 74 based on the information of the length of the light guide and the information of the main wavelength of the light source.

In the first embodiment described above, the additional light source 74 that emits the violet light LV is provided as a blood vessel information acquisition semiconductor light source for acquiring blood vessel information of the living tissue. However, instead of the additional light source 74 or in addition to the additional light source 74, another blood vessel information acquisition semiconductor light source may be provided. For example, in order to acquire the oxygen saturation of blood hemoglobin as blood vessel information, a semiconductor light source that emits narrow band blue light having a centroid wavelength of 473±10 nm may be provided. Undoubtedly, in a case where blood vessel information observation is not performed, only the blue, green and red semiconductor light sources may be provided without providing the blood vessel information acquisition semiconductor light source.

In the first embodiment described above, an LED is used as a light source. However, instead of the LED, semiconductor light sources, such as a laser diode (LD), may be used.

In the first embodiment described above, in the blood vessel emphasis observation mode, mixed light of the white light LW and the violet light LV is emitted to the observation part. However, violet light and green light or blue light and green light may be emitted to the observation part to acquire the blood vessel emphasis observation image.

In the first embodiment described above, light beams of a plurality of colors are simultaneously emitted to the observation part. However, the light beams of a plurality of colors may also be sequentially emitted to separately image the light of each color. In this case, it is preferable to use a monochrome imaging element as the image sensor 48.

In the first embodiment described above, the light source device and the processor device are separately configured. However, the light source device and the processor device may be configured as one device. The invention can also be applied to a fiber scope that guides the reflected light of the observation part of the illumination light using an image guide, an endoscope system using an ultrasound endoscope in which an imaging element and an ultrasound transducer are built into the distal end portion, and a light source device for an endoscope used for the same.

In the first embodiment described above, the invention is implemented in the endoscope system in which the endoscope 12 including the image sensor 48 is inserted into the subject to observe the inside of the subject. However, the invention is also suitable for a capsule endoscope system.

EXPLANATION OF REFERENCES

10: endoscope system
12: endoscope
12a: insertion part
12b: operation unit
12c: bending portion
12d: distal end portion
12e: angle knob
13a: zoom operation unit 13b: mode selector switch
14: light source device
16: processor device
18: monitor
19: console
20: light source unit
21: light source driving unit
22: light source control unit
23: light source information storage unit
24: table storage unit
25: correction amount storage unit
30a: illumination optical system
30b: imaging optical system
32: scope information storage unit
41: light guide
45: illumination lens
46: objective lens
47: zoom lens
48: image sensor
54: image acquisition unit
56: DSP
58: noise reduction section
59: conversion section
61: image processing unit
66: display control unit
69: control unit
71: first light source
72, 72b: second light source
73: optical filter
74: additional light source
75: third light source
76, 77, 99: multiplexing member
81, 83, 83b, 86, 88: light emitting element
82, 85, 87, 89: lens
84: phosphor
91, 92, 93, 97: photodetector
94, 95, 96, 98: beam splitter

What is claimed is:

1. An endoscope system, comprising:
an endoscope that has a light guide for guiding light;
two or more light sources that supply light to the light guide and have different main wavelengths;
a light source driving circuit that supplies a driving signal to each of the two or more light sources to emit light;
a light source control unit, comprising a processor, that inputs a light amount setting value to the light source driving circuit to make the light source driving circuit generate the driving signal corresponding to the light amount setting value for each light source; and
a light source information storage unit, comprising a first memory, that stores information of the main wavelength of at least one of the two or more light sources,
wherein the endoscope has a scope information storage unit, comprising a second memory, that stores information of a scope type, and
the light source control unit is configured to adjust a light amount ratio of the two or more light sources to a preset light amount ratio while adjusting a total amount of light emitted from a distal end of the endoscope to a preset light amount, by acquiring the information of the main wavelength of at least one of the light sources stored in the light source information storage unit, acquiring the information of the scope type from the scope information storage unit, setting at least one light amount setting value according to at least the information of the main wavelength of the at least one of the light sources stored in the light source information storage unit and information of a length of the light guide obtained from the information of the scope type, and inputting the light amount setting value to the light source driving circuit to control a light emission amount of the at least one of the light sources driven by the light source driving circuit.

2. The endoscope system according to claim 1,
wherein the endoscope has an illumination lens disposed on a distal end side of the light guide, and
the light source control unit sets the light amount setting value according to at least the information of the length of the light guide, information of the illumination lens obtained from the information of the scope type, and the information of the main wavelength of the light source.

3. The endoscope system according to claim 2,
wherein the light source control unit sets the light amount setting value according to at least the information of the length of the light guide, information of a type of the light guide obtained from the information of the scope type, and the information of the main wavelength of the light source.

4. The endoscope system according to claim 3,
wherein at least one of the two or more light sources is a blue light source that emits blue light, and
the light source control unit sets the light amount setting value for the blue light source.

5. The endoscope system according to claim 4,
wherein the light source control unit sets the light amount setting value according to an individual difference of at least one of the light sources.

6. The endoscope system according to claim 5,
wherein the endoscope is detachably connected to a light source device including the two or more light sources.

7. The endoscope system according to claim 6,
wherein the main wavelength of the light source is a centroid wavelength or a peak wavelength.

8. The endoscope system according to claim 1,
wherein the light source control unit sets the light amount setting value according to at least the information of the length of the light guide, information of a type of the light guide obtained from the information of the scope type, and the information of the main wavelength of the light source.

9. The endoscope system according to claim 1,
wherein at least one of the two or more light sources is a blue light source that emits blue light, and
the light source control unit sets the light amount setting value for the blue light source.

10. The endoscope system according to claim 1,
wherein the light source control unit sets the light amount setting value according to an individual difference of at least one of the light sources.

11. The endoscope system according to claim 1,
wherein the endoscope is detachably connected to a light source device including the two or more light sources.

12. The endoscope system according to claim 1,
wherein the main wavelength of the light source is a centroid wavelength or a peak wavelength.

* * * * *